(12) United States Patent
Hoffman et al.

(10) Patent No.: US 6,907,138 B1
(45) Date of Patent: Jun. 14, 2005

(54) METHOD AND DEVICE FOR ANALYZING SURFACE STRUCTURE

(75) Inventors: Peter Klaus Hoffman, Bochum (DE); Ludwig Eckert, Rödles (DE); Sebastian Tölg, Herdecke (DE); Marianne Andres, Bochum (DE); Robert Husemann, Essen (DE)

(73) Assignee: Invision Technologies AG, Bochum (DE)

( * ) Notice: Subject to any disclaimer, the term of this patent is extended or adjusted under 35 U.S.C. 154(b) by 0 days.

(21) Appl. No.: 09/445,967

(22) PCT Filed: Jun. 15, 1998

(86) PCT No.: PCT/EP98/03602

§ 371 (c)(1),
(2), (4) Date: May 1, 2000

(87) PCT Pub. No.: WO98/58242

PCT Pub. Date: Dec. 23, 1998

(30) Foreign Application Priority Data

Jun. 27, 1997 (DE) .......................................... 197 25 633

(51) Int. Cl.⁷ ................................................ G06K 9/00
(52) U.S. Cl. ....................................... 382/154; 382/312
(58) Field of Search ................................. 382/154, 108, 382/159, 285, 312, 318, 321; 356/625, 394, 475, 462

(56) References Cited

U.S. PATENT DOCUMENTS

| | | | |
|---|---|---|---|
| 4,162,126 A | * 7/1979 | Nakagawa et al. | ...... 430/288.1 |
| 4,988,202 A | 1/1991 | Nayar et al. | |
| 5,064,291 A | 11/1991 | Reiser | |
| 5,140,463 A | * 8/1992 | Yoo et al. | .................... 359/559 |
| 5,791,346 A | * 8/1998 | Craine et al. | ............... 600/407 |
| 5,812,265 A | * 9/1998 | Hoshiyama | .................. 356/625 |
| 5,949,389 A | * 9/1999 | Brown | ........................... 345/9 |

FOREIGN PATENT DOCUMENTS

| | | |
|---|---|---|
| DE | 4243863 | 6/1994 |
| DE | 4313258 | 10/1994 |
| DE | 43 13 258 | 10/1994 |
| DE | 4312452 A1 | 11/1994 |
| EP | 0 452 905 | 10/1991 |
| JP | 06058731 | 3/1994 |
| WO | WO94/14053 | 6/1994 |

* cited by examiner

*Primary Examiner*—Phuoc Tran
(74) *Attorney, Agent, or Firm*—IP Strategies

(57) ABSTRACT

The invention relates to a method for analyzing properties of a surface by taking an image scene with a camera, wherein at least two images are taken with an illumination with directed and/or diffused light, wherein the image information of the single images is converted into digital signals, and subsequently a three-dimensional image is determined from the digital signals in computer-aided manner. Further, the image relates to an image-taking device for performing this method, comprising a video camera and a lighting appliance being associated with the video camera, the lighting appliance comprising a first lighting system generating diffused light and a second lighting system generating directed light, and a controller through which the first and the second lighting systems are controllable electronically and independently from one another. Furthermore, the invention relates to a system for performing the above-identified method comprising an image-taking device of the above kind, a video card for digitizing image information taken with the image-taking device, a data storage for storing the digitized image information, and a processing device for computer-aided determination of a three-dimensional image of the stored image information.

19 Claims, 3 Drawing Sheets

METHOD AND DEVICE FOR ANALYZING SURFACE STRUCTURE

FIELD OF THE INVENTION

The invention relates, on the one hand, to a method and, on the other hand, to an apparatus for analyzing surface properties.

BACKGROUND OF THE INVENTION

In a plurality of medical, biological and technical applications, an analysis of surface properties is performed, for example, in dermatology for diagnosing skin cancer, or when inspecting surfaces of technical objects.

BRIEF SUMMARY OF THE INVENTION

In this context, the prior art comprises microscopes for manual use which facilitate a top illumination microscopy or aximutal microscopy of the surface to be analyzed. Such apparatus is a hand-held device comprising a microscope lens which, being coupled to a camera, facilitates an inspection and an evaluation of the surface. The images can be inspected on a monitor in enlarged form.

Video microscopes known in the art provide a two-dimensional image of the examined surface. A three-dimensional impression and the drawing of conclusions regarding the three-dimensional structure of the surface together with an analysis of the same is not possible.

DE 4243863 A1 discloses a method for analyzing the properties of a surface by taking an image scene with a camera, wherein at least two images are taken with illumination with directed light, the image information of the single images is converted into digital signals, and, subsequently, the structure of a surface, particularly the ragularity thereof, is determined in a computer-aided manner.

DE 4312452 A1 discloses a method for analyzing the properties of a surface by taking an image scene with a camera, wherein at least two images are taken with an illumination with directed light, the image information of the single images is converted into digital signals and, subsequently, quality determining parameters of the surface structures are calculated in a computer-aided manner.

DE 4313258 A1 discloses a method for analyzing the properties of a surface (texture of a human skin or a replica thereof) by taking an image scene with a camera, wherein at least two images are taken with illumination with directed light, the image information of the single images is converted into digital signals, and, subsequently, characteristic parameters are determined in a computer-aided manner.

DE 4312452 A1 further discloses an apparatus for analyzing the properties of a surface by taking images with a camera, comprising an image sensor, as for example, a matrix camera, with an illumination device assigned to the camera, light sources emitting directed light being arranged in the illumination device and being electronically controllable by a controller, as well as with a data storage for storing the image information digitized with a video card.

A similar apparatus is known from DE 4243863 A1.

In view of the prior art, the problem underlying the invention is to provide a method which facilitates an analysis of the three-dimensional properties and form of a surface.

This problem is solved by a method comprising the features of claim 1.

Further advantageous embodiments of the method in accordance with the invention are characterized in the subsidiary claims 2–4.

An essential point of the invention is that the properties of a surface are analyzed by taking an image scene of the surface, wherein at least two images are taken with different types of illumination. Herein, two images are taken either with an illumination in which the light impinges on the surface to be analyzed from two different directions, or one image is taken with directed light impinging under a predetermined angle onto the surface to be examined, and a further image is taken with diffuse illumination.

When taking the images, it is important to use a uniform brightness and color temperature for all types of illumination. This is achieved by a combined control of the power supply of the light sources and the shutter speed of the camera.

The geometrical distance between the surface to be examined or the subject and the lens is predetermined such that object and lens or camera are a fixed unit. The image direction, i.e. the camera position, is maintained. It is essential that at least two different images are taken using different types of illumination. The single images can be taken in a time sequence. Each image taken is digitized and the information is stored in a storage for further processing.

The three-dimensional structure of the surface is determined from the digitized image information. In doing this, photometric spatial calculations ere performed.

For determining the three-dimensional structure and texture, it is sufficient to take at least two images with directed illumination, as claimed in claim 2

In doing this, two images are taken with illumination from different directions. Even though taking two images is, in principle, sufficient, the analysis and the result is improved with further images, each of them taken with an illumination from another direction.

Using two light sources, they should be preferably arranged such that they are opposed to each other. This is possible if they are on a circle spaced apart from one another in a circumferential direction, said circle being perpendicular to the optical axis. Further, the light sources are aligned at an angle converging to the optical axis. Then, the surface to be inspected is illuminated during image talking from two different directions, such that a sharp contrast is formed at the illuminated side and the corresponding peripheral sides while a weak contrast and/or a shadow is formed in the rear area. Then, by performing operations to combine the information gained from the images, such as gray-scale subtraction, it is possible to draw conclusions regarding the three-dimensional information of a surface irregularity.

During analysis, it is important that at least two, preferably more, images are taken with different illumination directions. The more that image information is obtained from the single images, the more precisely that the three-dimensional structure can be determined.

Light sources in the form of miniaturized light bulbs or light-emitting diodes can be used. The illumination direction can be obtained by respective alignment of the light sources.

A logic circuit, incorporated with the control program, insures a uniform basic brightness and color temperature for all illumination modes. This is obtained by the combined control of the power supply of the light sources and of the shutter speed of the camera. Time critical color applications require a three-chip color camera. In color applications which are not time critical, the three-chip color camera can be replaced by a cheaper gray-scale camera. In this case, the light sources can be embodied in the form of light diodes which, depending on the control, emit light in the rod, green or blue spectral range.

In this case, three images with the different-colored illuminations are required to replace an RGE image of the three-chip color camera.

As already discussed, the three-dimensions structure and texture of a surface is determined from the images taken with directed light. In this case, it is important to use light which is as directed as possible. It is understood that the expression "structure" refers to the macroscopic form, and that the term "three-dimensional texture" refers to the microscopic structure of the surface.

In accordance with the features of claim 3, at least one image is taken with directed light and one image is taken with diffused light.

The data obtained from the image taken with diffused light are for determining the texture of the surface with respect to brightness and color. In this case, it is particularly possible to analyze the reflectivity of a surface. For this purpose the illumination has to be as uniform as possible and should not produce shadows.

In accordance with the features of claim 4, the determined three-dimensional structure is classified with an algorithm which has been trained with given feature combinations.

This analysis is performed depending on the surface to be examined and the specific features under consideration.

Examples for the use of the method of the invention are dermatology, metallography, material sciences, inspection of circuit boards, or criminology. In dermatology, an inspection and diagnosis of skin coloring or melanomas are performed. In material science, the method can be used for examining welded joints or for diagnosing cracks in metallic structures. In criminology, the examination of hair, fibers, and similar traces can be further improved.

The evaluation is performed by extraction of certain application-specific features from the determined three-dimensional information. When analyzing a welded joint, threshold operations might be sufficient. In complex applications, as for example skin cancer diagnosis, the evaluation can be performed with a neural network.

Information obtained from a three-dimensional image can be evaluated with respect to points of higher information content wherein the net is trained in a different manner depending on the application, such that specific, prominent feature combinations can be selected.

In skin-cancer diagnosis, the image data are analyzed in dependence with the so-called ABCDE rule with respect to asymmetric edging, fuzzy boundary, dark or inhomogeneous coloring, diameter as well as elevation relative to the normal skin surface.

Image processing can be divided into three main steps. These steps are pre-processing, the segmentation of the zones of interest and the extraction and analysis of the features.

In pre-processing, sensor artifacts in digital images, such as reflections, noise and the like, are removed. In this case, non-linear filters are used, since known low-pass filters influence important information, for example, information on skin folds.

The segmentation of zones of interest is obtained with edge detectors, contour finders, and the combined estimation of local and global color distributions, with post-processing performed by the self-learning neural network. By doing so, the content of the image is restricted to the area in which a candidate for a tumor is present. In this area, analysis of features as such can be performed. Some features, such as size and diameter, are derived directly from the segmentation. This segmentation also allows conclusions regarding the asymmetry of the lesion.

The features extracted in this way are classified with a trained artificial neural network in which histological results are used as verification. External data, as, for example, the total number of birth marks or moles, the familial medical history, the skin type and the like, can be included in the neural network.

In this way, a dermatological examination with a high examination and diagnosis accuracy is possible.

Further, it is an object underlying the invention to provide an image-taking apparatus providing images which are necessary for performing the method of the invention.

This object is achieved with an image-taking apparatus with the features of claim 5.

Furthermore, it is an object underlying the invention to provide an apparatus to perform the method.

This object is achieved by an apparatus as claimed in claim 3.

The image-taking apparatus in accordance with the invention comprises a handpiece in the form of a video camera with a lighting appliance being assigned thereto. Light sources for providing directed and diffused light are arranged in the lighting appliance. The controlled activation of the single light sources in the single images is performed by an electronic control. Control of the illumination is synchronized with the taking of the image of the video camera such that the image sequence can be taken in a time-optimized manner.

In the arrangement of the invention, a video card is included which digitizes the images taken by the video camera. The digitized image information is stored in a data storage. Automatically, data processing can be performed in processing means.

The image taking device comprises a switchable illumination which is synchronized with the image taking.

The lighting appliance is essential for the invention. Using miniaturized light sources allows the integration of different illumination effects (diffuse illumination, directed illumination from different angles, and shine-through illumination) in the lighting appliance. The lighting appliance is detachably assigned to the video camera in the form of an ancillary element for the camera. Using the lighting appliance, it is possible to take video images with at least two different types of illumination, the remaining image-taking parameters, such as camera position or geometric distance and orientation of the surface with respect to the lens, being maintained or unchanged. In this way, images with directed or diffused illumination can be taken and, by comparing the same, extraction of a three-dimensional image is possible.

Diffused light can be obtained by assigning a diffusing device to some of the light sources in the lighting appliance, as claimed in claim 6. Such a diffusing device can be obtained by apertures arranged in front of the light sources, such that only light which is reflected from inner wells of a tubular lighting appliance and thereby made diffuse, impinges on the object to be imaged. In this way, reflected light can be avoided.

A further advantageous embodiment of the image-taking device in accordance with the present invention is characterized by the features of claim 7.

Accordingly, at least two light sources are arranged on a circle in spaced-apart relationship from one another and in circumferential direction, said circle being perpendicular to the center longitudinal axis of the lighting appliance, and said light sources being arranged under an angle converging to the center longitudinal axis.

In doing so, the taking of images with an illumination from different directions is possible. In this connection, the position of the camera is maintained.

By illuminating the object from different directions, the taking of images with different contrast and shadow zones is possible. Thereby, conclusions can be drawn regarding the three-dimensional irregularity of the surface by subtraction of gray levels.

In the arrangement with two light sources for directed illumination, it is advisable to arrange the two light sources on a circle spaced apart by 180°. Regarding the projection angle, a setting between 5° and 45° with respect to the optical axis of the light source in relation to the surface to be analyzed is considered as advisable. The arrangement of the lighting appliance with an angle of 45° converging to the center longitudinal axis allows, from a technical point of view, a universal application. By doing so, both elevations and depressions as well as the texture of a surface irregularity can be determined.

In principle, it is an advantage for determining the contour of a surface irregularity. If the surface is illuminated in a grazing manner. For taking the single images, the light is directed from different sides obliquely onto the surface to be examined. An acute angle with respect to the surface, such as, for example, 10°, is advantageous.

To draw conclusions about the three-dimensional irregularity of a surface, is sufficient to take two images with an illumination from different directions. The result, however, is improved if more than two, preferably three to six, images are taken with a different illumination direction. Accordingly, in an advantageous embodiment of the lighting appliance, a plurality of light sources for generating directed light is evenly arranged on the circle.

An advantageous embodiment is provided in accordance with claim 8 in which different ancillary rings can be applied onto the lighting appliance. For example, an ancillary ring comprising a white slice provides a standardized white balance of the camera. Further, an ancillary ring comprising the function of a spacer with respect to the surface to be examined can be used. Further, in contact dermatoscopy another ancillary ring for an epiluminescent microscopic image can be used comprising a coated glass slice being an anti-reflecting filter for polarized light.

In the following, the invention is described referring to embodiments shown in the drawings in which:

BRIEF DESCRIPTION OF THE DRAWINGS

In FIGS. 1–3, the arrangement of a video camera 1 above a surface 2 to be analyzed comprising a surface irregularity 3 in form of an elevation 4 is shown.

Figure 3:
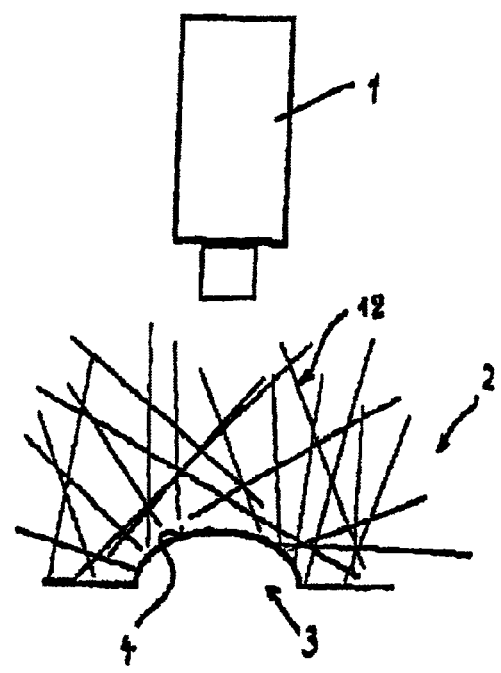

For analyzing the properties of the surface 2, two images are taken with an illumination with directed light (FIGS. 1 and 2) and one image is taken with an illumination with diffused light (FIG. 3). The image information is converted into digital signals from which a three-dimensional image of the elevation 4 is determined in a computer-aided manner.

The position of the video camera 1 remains constant during the diagnosis process such that the geometric distance between the surface 2 and the lens of the camera remains constant.

DETAILED DESCRIPTION OF THE INVENTION

Figures 1, 2:
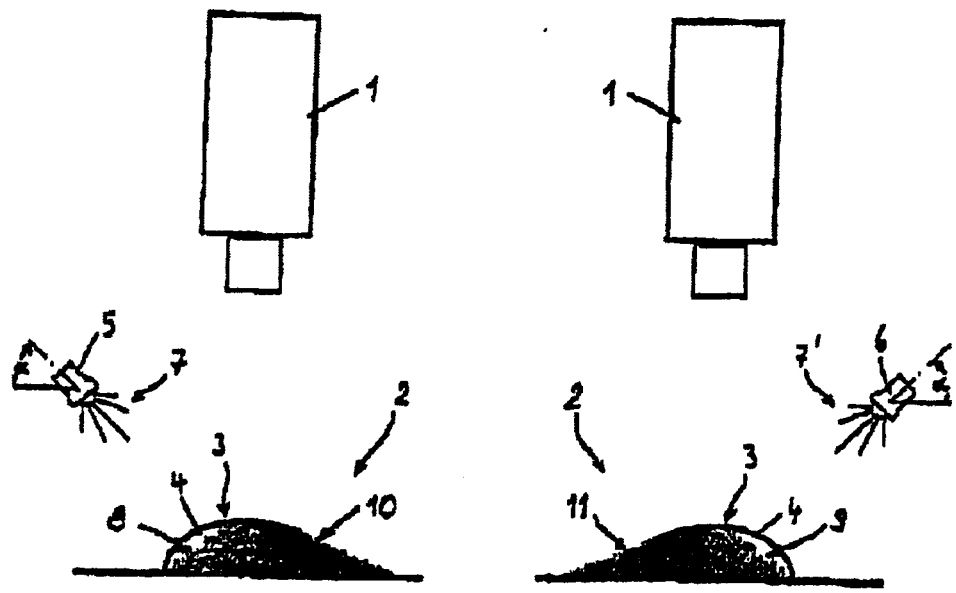
FIGS. 1–3 show a schematic diagram of the arrangement of a camera and different light sources with respect to a surface to be analyzed.

In FIGS. 1–3, the arrangement of a video camera 1 above a surface 2 to be analyzed comprising a surface irregularity 3 in form of an elevation 4 is shown.

Furthermore, an image is taken using diffused illumination. The light rays which illuminate the surface 2 diffusely are denoted in FIG. 3 with reference numeral 12.

The digitized signals of the three images are processed and analyzed in a computer by a combination of operations such that three-dimensional information of the surface to be analyzed is obtained.

In the next step, the analysis of the surface 2 and/or the surface irregularities 3 obtained in the above manner can be performed.

Figure 4:
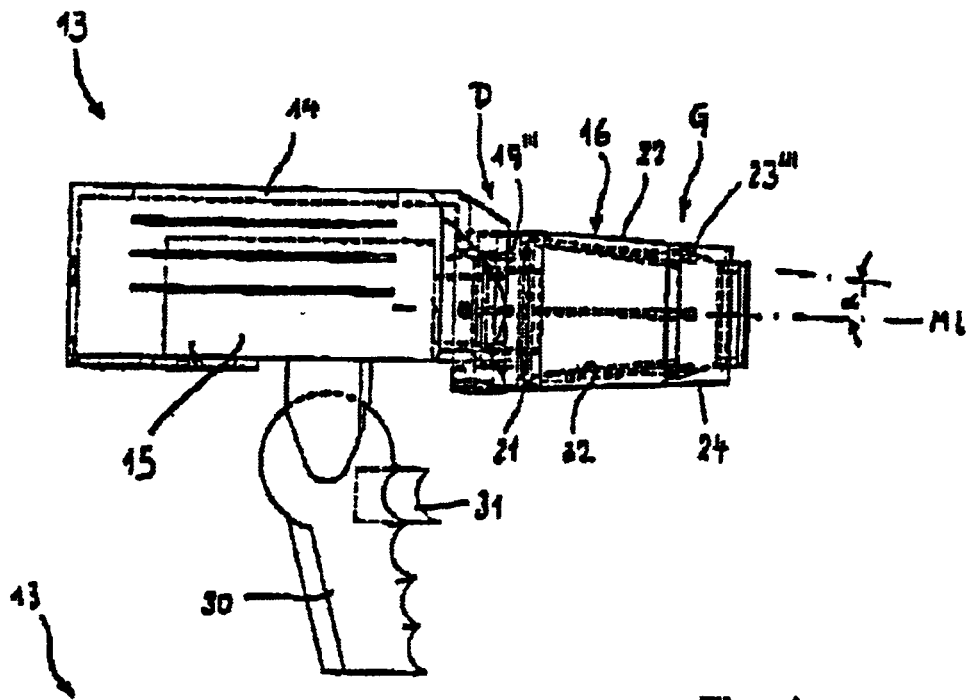
FIG. 4 shows a slide view of a surface diagnosis apparatus.
Figure 5:
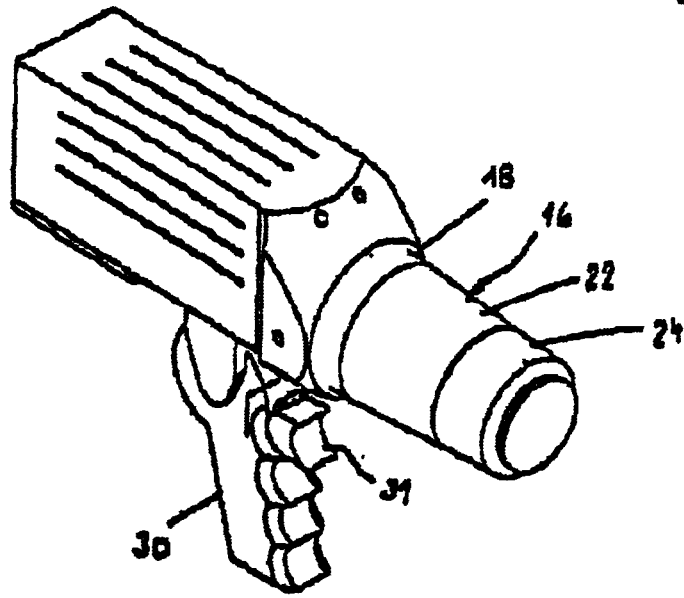
FIG. 5 shows the surface diagnosis apparatus in a perspective view.
Figure 6:
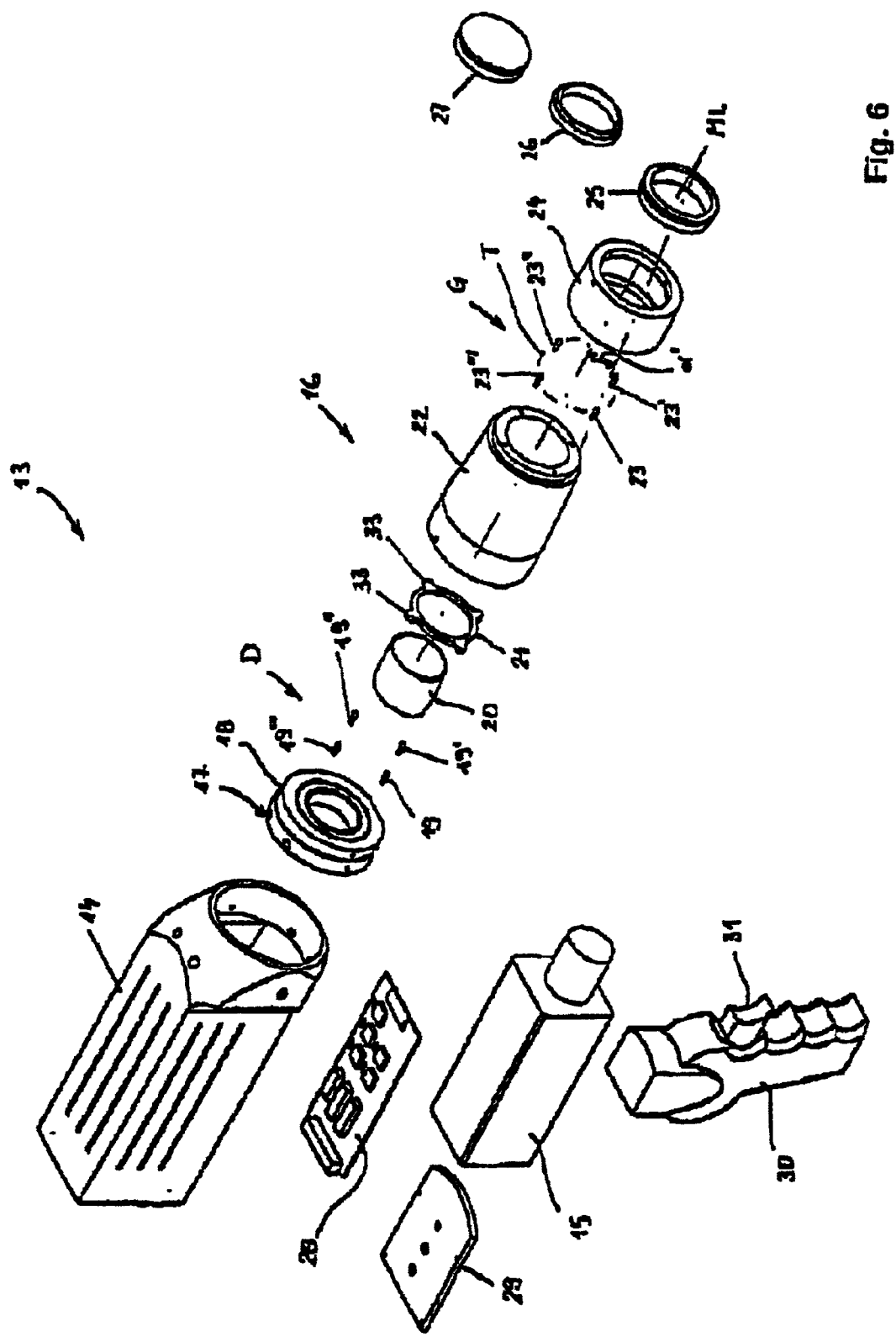
FIG. 6 shows the surface diagnosis apparatus in exploded view.

In FIGS. 4–6, a surface diagnosis apparatus 13 is described. In all three Figures, the corresponding parts are denoted with the same reference numerals.

The surface diagnosis for apparatus 13 comprises a video camera 15 being provided in a housing 14 having a lighting appliance 16 being associated therewith. The lighting appliance 16 is detachably coupled with the housing 14.

The lighting appliance 16 comprises a camera adapter 17 and a rear illumination tubs 18. The tube comprises four light sources 19, 19', 19", 19'". The light sources 19, 19', 19", 19'" establish a first lighting system 0 for generating diffused light.

By interposing a spacer element 20 and a dimmer ring 21, the rear illumination tube 18 is connected to a medium illumination tube 22.

The medium illumination tube 22 comprises four further light sources, 23, 23', 23", 23'". The light sources 23, 23', 23", 23'" establish a second lighting system G for generating directed light.

The head of the lighting appliance 16 is established by a front illumination tube 24.

The reference numerals 25, 26, 27 in FIG. 6 denote three different ancillary rings which can be applied onto the lighting appliance.

A control circuit board 28, being coupled to the fighting system D and G, is applied to the video camera 15. Via the circuit board 28, the lighting systems D and G or their light sources 19, 9', 19", 19'" and 23, 23', 23", 23'" are controlled.

Further, a calibration of the different illumination modes is provided by the circuit control board 28.

Reference numeral 29 denotes a ground plate of the surface diagnosis apparatus 13. The surface diagnosis apparatus 13 is held and operated via a handpiece 30 in which a shutter release 31 is integrated.

The front lighting system G comprises four light sources 23, 23', 23", 23'". These light sources are provided on a circle T being perpendicular with respect to the center longitudinal axis ML of the lighting appliance 16, and being spaced apart with respect to one another by 90° in circumferential direction.

Further, the light sources 23, 23', 23", 23''' are arranged with an angle α converging with respect to the canter longitudinal axis ML. Switched on one at a time, the light sources provide a directed illumination which is necessary for the photometrical spatial calculation process.

The lighting system D for producing diffused light is provided in the rear illumination tube 18. In the shown embodiment, the lighting system D comprises four light sources 19, 19', 19", 19'''. Using the dimmer ring provided in front of the light sources, only light reflected from the inner wall 32 of the middle illumination tube 22, which became diffused thereby, impinges on the surface to be analyzed. For doing so, the dimmer ring 24 comprises four dimmer elements which extend beyond the outer circumference of the ring.

The lighting systems D and G can be used together, for example, for contact dermatoscopical image-taking. Such a diagnosis process is described in the following.

In the beginning of the diagnosis, the ancillary ring 26 is applied to the illumination appliance 16. The ancillary ring 26 is an open ring comprising the function of a spacer when taking images with diffused and directed illumination.

The surface diagnosis apparatus is brought in full contact with the skin surface to be examined via the surfaces of the ancillary ring 26. On a monitor (not shown) of a computer, a diffuses illuminated real image of the skin surface appears. By operating the shutter release 31 in the handle 30, images are taken with diffused and directed illumination.

Image 1 is taken with diffused illumination. Therefore all four light sources 19, 19', 19", 19''' are activated. Then, four images with directed illumination are taken. The single images are taken in time intervals of 200 ms, wherein for each image, a different light source 23, 23', 23", 23''' is activated.

After approximately 1 second, the single images appear for inspection on the monitor. Should the quality of an image be insufficient, then the user can repeat the whole image-taking procedure. Otherwise, he/she is requested to substitute the auxiliary element 26 with the auxiliary element 27. Auxiliary element 27 contains a coated glass serving as a filter for polarized light or against unintended reflections. With the auxiliary element 27, a contact dermatoscopical image is taken. Then, a request for the quality is issued. Should the quality of this image also be positive, the image-taking process is completed.

The six images taken are digitized and stored in a data base which comprises additional risk data of the patients. Using image processing algorithms, the features are extracted from these images. The features together with the risk data are used as data bases for a neural network which is trained to distinguish between benign pigment moles from malignant pigment moles. Using the neural algorithm, a value for the malignancy of the pigment mole is determined. The surface structure of the skin in the area of the pigment mole is used as an important feature for the automatic skin cancer diagnosis performed with the hand-held surface diagnosis apparatus 13.

What is claimed is:

1. A method for analyzing properties of a surface comprising:
   taking an image scene with a camera by taking at least a first image of the surface while illuminating the surface with directed light from a first direction and taking at least a second image of the surface while illuminating the surface with directed light from a second direction, thereby providing image information corresponding to each said image; converting wherein the image information corresponding to each said image into respective digital signals; and determining a three-dimensional image from the digital signals in a computer-aided manner.

2. The method of claim 1, wherein further comprising classifying the three-dimensional image according to an algorithm that has been trained with predetermined feature combinations.

3. The method of claim 2, wherein classifying the three-dimensional image according to an algorithm includes training the algorithm using a neural network.

4. The method of claim 1, wherein the surface is a surface of biological tissue.

5. The method of claim 1, wherein determining a three-dimensional image from the digital signals in a computer-aided manner includes applying gray-scale subtraction to combined image information represented by the digital signals.

6. The method of claim 1, wherein determining a three-dimensional image from the digital signals in a computer-aided manner includes applying gray-scale subtraction to combined image information represented by the digital signals.

7. An image-taking device that performs the method of claim 1, comprising:
   a video camera; and
   a lighting appliance that provides illumination for the video camera;
   wherein the lighting appliance comprises a lighting system including at least two light sources that generate directed light, and a controller that electronically controls the at least two light sources independently.

8. The image-taking device of claim 7, wherein the at least two light sources are arranged on a circumference of a circle, wherein said circle is perpendicular to a center longitudinal axis of the lighting appliance, and wherein said light sources are arranged at angles directed to converge at the center longitudinal axis.

9. The image-taking device of claim 7, wherein the lighting appliance further comprises at least one ancillary ring disposed between the video camera and the surface, wherein the at least one ancillary ring is at least one of a spacer and a filter.

10. A system that performs the method of claim 1, comprising:
    an image-taking device, comprising:
    a video camera that captures image information; and
    a lighting appliance that provides illumination for the video camera;
    wherein the lighting appliance comprises a lighting system including at least two light sources that generate directed light, and a controller that electronically controls the at least two light sources independently;
    a video card that digitizes the image information captured by the image-taking device;
    a data storage that stores the digitized image information; and
    a processing device that generates a computer-aided determination of a three-dimensional image based on the stored digitized image information.

11. A method for analyzing properties of a surface, comprising:
    taking an image scene with a camera by taking at least one image while illuminating the surface with directed light from a direction that is oblique with respect to an optical axis that is normal to the surface, and taking at least another image while illuminating the surface with diffused light, thereby providing image information corresponding to each said image;

converting the image information corresponding to each said image into respective digital signals; and determining a three-dimensional image from the digital signals in a computer-aided manner.

12. The method of claim 11, further comprising classifying the three-dimensional image according to an algorithm that has been trained with predetermined feature combinations.

13. The method of claim 12, wherein classifying the three-dimensional image according to an algorithm includes training the algorithm using a neural network.

14. The method of claim 11, wherein the surface is a surface of biological tissue.

15. An image-taking device that performs the method of claim 11, comprising:

a video camera; and a lighting appliance that provides illumination for the video camera;

wherein the lighting appliance comprises a first lighting system that generates diffused light, a second lighting system that generates directed light, and a controller that electronically controls the first lighting system and the second lighting system independently.

16. The image-taking device of claim 15, wherein the first lighting system comprises light sources that provide light, and a scattering device that scatters the light provided by the light sources.

17. The image-taking device of claim 15, wherein the second lighting system comprises at least two light sources that are arranged on a circumference of a circle, wherein said circle is perpendicular to a center longitudinal axis of the lighting appliance, and wherein said light sources are arranged at angles directed to converge at the center longitudinal axis.

18. The image-taking device of claim 15, wherein the lighting appliance further comprises at least one ancillary ring disposed between the video camera and the surface, wherein the at least one ancillary ring is at least one of a spacer and a filter.

19. A system that performs the method of claim 11, comprising:

an image-taking device, comprising:

a video camera that captures image information; and a lighting appliance that provides illumination for the video camera;

wherein the lighting appliance comprises a first lighting system that generates diffused light, a second lighting system that generates directed light, and a controller that electronically controls the first lighting system and the second lighting system independently;

a video card that digitizes the image information captured by the image-taking device;

a data storage that stores digitized image information; and a processing device that generates a computer-aided determination of a three-dimensional image based on the stored digitized image information.

* * * * *

UNITED STATES PATENT AND TRADEMARK OFFICE
CERTIFICATE OF CORRECTION

PATENT NO. : 6,907,138 B1
DATED : June 14, 2005
INVENTOR(S) : Peter Klaus Hoffman et al.

It is certified that error appears in the above-identified patent and that said Letters Patent is hereby corrected as shown below:

<u>Title page,</u>
Item [73], Assignee, change "Invision Technologies AG" to -- ZN Vision Technologies AG --.

Signed and Sealed this

Sixth Day of September, 2005

JON W. DUDAS
*Director of the United States Patent and Trademark Office*